United States Patent [19]
Tennis et al.

[11] Patent Number: 5,349,967
[45] Date of Patent: Sep. 27, 1994

[54] SHIELD FOR USE BY HEALTH CARE PERSONNEL DURING SKIN INJECTIONS

[76] Inventors: John M. Tennis, 121 Fawnbrook Dr., Greenwood, S.C. 29646; Adriane H. Able, Rte. 3, Box 769, Saluda, S.C. 29138; Marilyn C. Coleman, 104 Spruce Ct., Milford Manor, Greenwood, S.C. 29649; Mark Hough, 156 Jamestowne Ct., Lexington, S.C. 29072; Kaye M. Mahon, Rte. 1, Hwy. 101, Gray Court, S.C. 29654

[21] Appl. No.: 33,837
[22] Filed: Mar. 19, 1993
[51] Int. Cl.$^5$ ............................................. A61G 13/00
[52] U.S. Cl. .................................... 128/888; 128/849; 132/73; 160/351; 160/352
[58] Field of Search ................. 128/849, 858, 888; 160/351, 352; 132/73

[56] References Cited

U.S. PATENT DOCUMENTS

| | | | |
|---|---|---|---|
| 1,642,385 | 9/1927 | Pryor | 160/351 X |
| 2,218,296 | 10/1940 | Perras | 160/351 X |
| 2,491,957 | 12/1949 | Dilley | 160/351 |
| 2,814,294 | 11/1957 | Figge | 604/49 |
| 3,194,235 | 7/1965 | Cooke | 128/888 |
| 3,490,448 | 1/1970 | Grubb | 604/51 X |
| 3,760,803 | 9/1973 | Boothby | 604/49 |
| 3,961,622 | 6/1976 | Edwards | 604/52 X |
| 4,043,701 | 8/1977 | Jaeger | 408/241 G |
| 4,314,568 | 2/1982 | Loving | 604/116 X |
| 4,362,157 | 12/1982 | Keeth | 604/116 |
| 4,755,170 | 7/1988 | Golden | 604/52 |
| 4,919,150 | 4/1990 | Grant | 128/877 |
| 4,936,318 | 6/1990 | Schoolman | 128/917 X |
| 4,967,775 | 11/1990 | Kaiser | 132/73 |
| 5,012,852 | 5/1991 | Blackhurst | 160/351 |
| 5,015,228 | 5/1991 | Columbus et al. | 604/51 |
| 5,018,534 | 5/1991 | Grant | 128/877 |
| 5,085,234 | 2/1992 | Silverman | 132/73 |

*Primary Examiner*—Steven A. Bratlie
*Attorney, Agent, or Firm*—Michael A. Mann

[57] ABSTRACT

A protective device having two transparent, spaced-apart shields held at an angle to one another. The device is symmetric so that either shield can serve as a base for the other and either can serve as a shield. When one of the shields is horizontal, the other shield is positioned at a suitable angle with respect to the practitioner's face to shield against contact with the patient's body fluids during medical procedures. The shields are held in cantilevered relation by a single support so that access to the space therebetween is maximized and so that the device can be oriented as dictated by the handedness of the user. The device is preferably formed from a single sheet of clear plastic folded twice to form the angled shields on either side of the support. The device may be used with minor surgical procedures and any medical procedure that involves venipuncture or arterial puncture.

20 Claims, 1 Drawing Sheet

U.S. Patent  Sep. 27, 1994  5,349,967
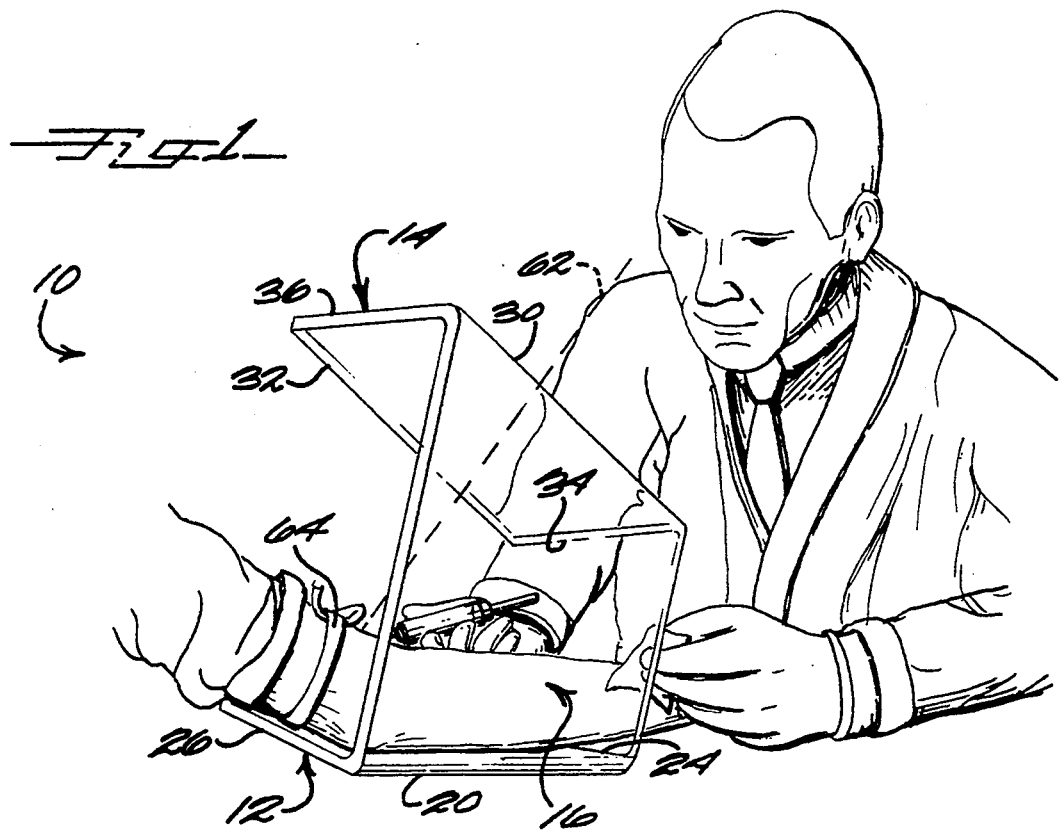
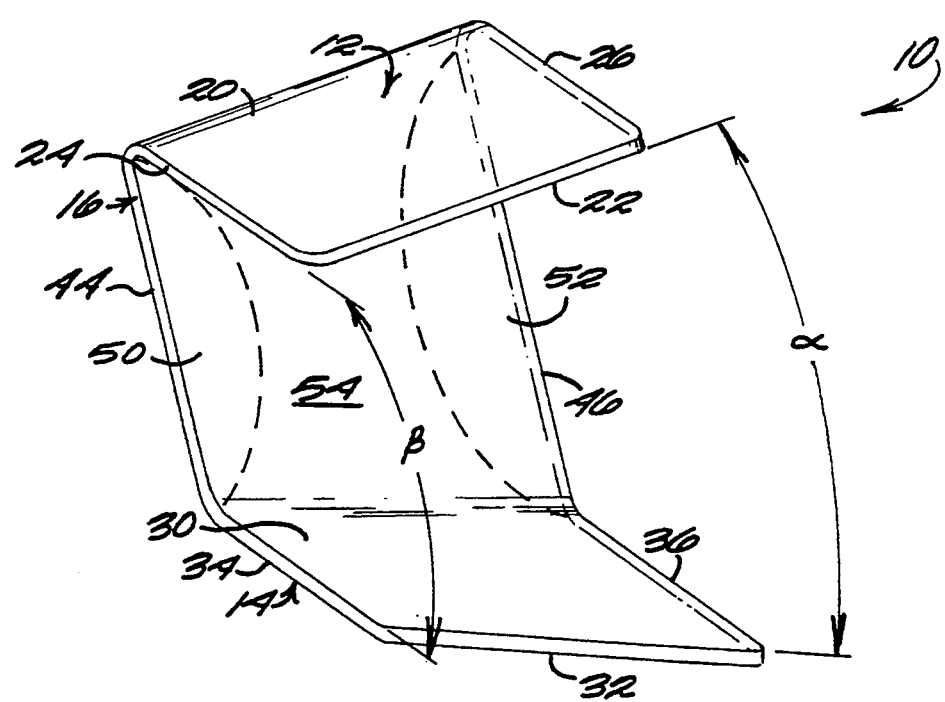

SHIELD FOR USE BY HEALTH CARE PERSONNEL DURING SKIN INJECTIONS

BACKGROUND OF THE INVENTION

1. Field of the Invention

The present invention relates to protection of health care personnel engaged in venipuncture or arterial puncture procedures. In particular, the invention relates to a shield and method for protecting medical personnel from the possibility of contact with a patient's body fluids during procedures that involve penetration of a vein or artery.

2. Discussion of Background

Devices such as hypodermic syringes and catheters are used for drawing blood from a patient for testing purposes, for intravenous administration of nutrients and medication, for monitoring blood pressure and blood gas, and so forth. Use of these devices frequently exposes medical practitioners to the patient's blood. For example, when using a conventional syringe to draw blood from a patient, the practitioner inserts the needle into a vein and retracts a plunger to create a vacuum inside the syringe. The vacuum causes blood to flow through the needle and into the body of the syringe. The needle is withdrawn after sufficient blood has been received in the syringe, often resulting in blood spurting out of the puncture site under pressure. Some blood may remain on the outer surface of the needle; some may spurt upwards onto the face or body of the practitioner.

Whenever a medical practitioner draws blood from a patient, there exists the possibility of contact with the blood leading to transmission of infectious or contagious diseases. This possibility is also present during other medical procedures that may involve contact with the patient's body fluids or tissues. Substances of concern include blood, saliva and other body fluids, small particles of skin, fat or muscle tissue, bone particles, and so forth. Such substances may carry hepatitis, acquired immune deficiency syndrome (AIDS), or other transmittable diseases. The substances may come into contact with an open cut, a mucous membrane, or the like of the practitioner such that he or she becomes infected or contaminated by the substances.

Medical personnel generally use surgical garments and masks for protection. "Moon suits" provide full-body coverage, but are cumbersome for use in performing routine tasks and minor surgical procedures. Typically, the practitioner's eyes and other exposed parts are not protected from contact with fluids in the form of airborne sprays, streams, or splashes.

A number of devices are available for use in making injecting or drawing blood safer. Columbus, et al. (U.S. Pat. No. 5,015,228) describes a device that prevents the spread of blood-borne diseases such as AIDS to hospital workers drawing blood. The needle is pushed through a "shield" made of a hydrogel laced with agar and copolymer of acrylamide crosslinked with a monomer. Figge (U.S. Pat. No. 2,814,294) teaches a pad with a central "placque" made of foam sponge for controlling bleeding during and immediately after injections, but not for protecting hospital workers. Grubb (U.S. Pat. No. 3,490,448) discloses a bandage that controls bleeding incident to an injection or taking a blood sample.

Various other devices are applied to the patient in connection with an injection or drawing blood to facilitate the procedure but not necessarily to protect medical personnel. These include a device for covering the tip of a needle to prevent "needle stick" (Golden, U.S. Pat. No. 4,755,170); a pair of plates or "ribs" that help to hold a vein in place for drawing blood (Loving, U.S. Pat. No. 4,314,568); a method of drawing blood from an infant's femoral artery using a device that assures that the needle is held at an optimum angle and pressure is applied to the skin (Edwards, U.S. Pat. No. 3,961,622); a clamp for elevating muscle tissue for an injection done by the patient (Boothby, U.S. Pat. No. 3,760,803); a template for making a series of injections over an area of the body such as might be done in the case of diabetes or allergy tests (Keeth, U.S. Pat. No. 4,362,157). These devices do not protect medical personnel from contact with blood or other body fluids.

Other devices that provide a physical barrier generally are obtrusive or do not prevent the escape of fluids. Thus, Schoolman (U.S. Pat. No. 4,936,318) provides a device that is placed between the face and hands of the practitioner. The device includes a transparent shield and a vacuum that aspirates blood and other fluids entrained in air to prevent the spread of AIDS. The shield is held on a frame that supports it above a patient on whom some procedure is being performed.

There is a need for a protective device that allows medical personnel to have relatively unobstructed manual access to a patient while minimizing the possibility of contact with the patient's blood. The device should be simple and inexpensive to manufacture, sterilizable, and usable in a wide range of medical procedures by either right-handed or left-handed users.

SUMMARY OF THE INVENTION

According to its major aspects and broadly stated, the present invention is a protective device having two spaced-apart, generally flat shields held by a holding means at an angle with respect to one another. The space between the shields is dimensioned for a portion of a patient's body to be positioned therein and to allow the user access for performing a medical procedure on the patient. The device is orientable so that either of the shields can be positioned between the user and the patient with the other shield then serving as a base. To allow the user a clear view of the site where the procedure is to be performed, the shields are transparent. Preferably, the device is formed from a single sheet of clear plastic folded twice to form the two shields at the proper angle so that when one shield is horizontal, in use as a base, the other is oriented to be approximately parallel to the plane of the face of the health care worker.

To use the device, it is positioned with one shield serving as a base and the patient's arm (or other body part on which a medical procedure is to be performed) in the region between the shields, resting on the base. The upper shield then protects the health care personnel from being splashed in the face by the patient's body fluids. However, the device allows the user a clear view and generally unobstructed working access to the patient.

The device maybe used with any medical procedure that involves the collection of blood or other body fluids, venipuncture for the administration of therapeutic intravenous agents, arterial puncture, catheterization, and minor surgical procedures such as wound or incision stitching or dressing.

The symmetry of the present invention is an important feature of the invention. Because of the orientation of the two shields with respect to each other, either can serve as a base or support for the other, and either can serve as a shield. When one of the shields is horizontal, the other shield is positioned at a suitable angle with respect to the user's face to shield against contact with the patient's body fluids. Consequently, a medical practitioner can use the device on either arm of a patient regardless of his or her hand preference.

The holding means is an important feature of the present invention for two reasons. First, it separates the two shields so that a patient's arm (or some other portion of the body) can be placed between them and the practitioner has access to the arm for performing the medical procedure. Second, it holds the shields at an angle selected so that, when one shield is horizontal, the other shield is at approximately the correct angle with respect to the user's face to shield most effectively against contact with body fluids, namely, approximately parallel to the plane of the face of the user.

Another feature of the present invention is the angle between the shields. The angle is chosen to effectively prevent the patient's blood or other body fluids from contacting the user's face, while allowing ready access to the region between the shields to perform a medical procedure. Therefore, the shields are nonparallel and preferably held at an angle between approximately 15 degrees and 75 degrees, and most preferably at an angle such that the uppermost shield is approximately parallel to the user's face during the procedure.

Still another feature of the present invention is the use of a single sheet of clear plastic to manufacture the device. In a preferred embodiment of the invention, a sheet of clear plastic is folded at right angles along two non-parallel lines to form the two spaced-apart, angled shields. The device is easy to make in this form and easily sterilized, having no surface features that may retain body fluids and other wastes.

Other features and advantages of the present invention will be apparent to those skilled in the art of medical procedures and safety from a careful reading of the Detailed Description of a Preferred Embodiment presented below and accompanied by the drawings.

BRIEF DESCRIPTION OF THE DRAWINGS

In the drawings,

FIG. 1 is a perspective view of a device according to a preferred embodiment, shown in use; and FIG. 2 is a perspective view of the device shown in FIG. 1 from the opposite side.

DETAILED DESCRIPTION OF A PREFERRED EMBODIMENT

Referring now to FIGS. 1 and 2, there is shown a protective device 10 according to a preferred embodiment of the present invention. Device 10 includes a first shield 12, a second shield 14 and support 16. Shield 12 has a first side 20, a second side 22, a first edge 24 and a second edge 26. Similarly, shield 14 has a first side 30, a second side 32, a first edge 34 and a second edge 36; support 16 has a first edge 44 and a second edge 46. Cutouts 50, 52, respectively, may be made in support 16 to increase access to the space between shields 12 and 14 by making the middle of support 16 smaller than shields 12 and 14 (see FIG. 2). Alternatively, edges 44 and 46 may be straight, as shown in FIG. 1. Shields 12 and 14 are substantially flat. Support 16 may be flat, or assume some other configuration if desired. Shields 12 and 14 and support 16 define a space or region 54 therebetween.

Support 16 is attached to first side 20 of shield 12 and first side 30 of shield 14. Shields 12 and 14 are supported only by support 16 on one side each. Thus, support 16 holds shields 12 and 14 in cantilevered relation. Cantilevered relation means that shields 12 and 14 are each held along one side by support 16, leaving the other sides of each unsupported but held in spaced relation by their attachment to support 16. Second sides 22, 32 of shields 12, 14, respectively, define an angle $\alpha$. Similarly, first edge 24 of shield 12 and first edge 34 of shield 14 define an angle $\beta$.

Angle $\alpha$ is chosen so as to substantially prevent the patient's blood or other body fluids from contacting the user's face, while allowing ready access to region 54 for performing a medical procedure. Therefore, shields 12 and 14 are nonparallel with $\alpha$ greater than 0 degrees and less than 90 degrees. Preferably, $\alpha$ is between approximately 15 degrees and 75 degrees. Most preferably, $\alpha$ is chosen so that, when the user is performing a procedure on a patient, a line 62 between the user's face and the operating site is approximately perpendicular to the upper shield, whether the upper shield is shield 12 or shield 14 (see FIG. 1). First edges 24 and 34 are preferably approximately parallel, with $\beta = 0$ degrees, and shields 12, 14 approximately perpendicular to support 16.

The dimensions of device 10 are chosen in view of the intended use of the device. Thus, for procedures performed on a patient's arm, first edges 24, 34 of shields 12, 14 may be approximately 6" (about 15 cm) long and approximately 7" (about 18 cm) apart. Second edges 26, 36 may be approximately 10" (about 25 cm) apart, and shields 12, 14 may be approximately 10"–12" (about 25–30 cm) long. It will be understood, however, that the dimensions of device 10 may vary without departing from the spirit of the present invention.

Device 10 is preferably manufactured from a single sheet of transparent plastic, folded to form two spaced-apart, angled shields 12 and 14 connected by shield 16. Device 10 is easy to manufacture in this form and to sterilize, having no surface features that can retain tissues or serve as breeding sites for microorganisms. Alternatively, shields 12 and 14 and support 16 may be formed separately and their edges attached by suitable means.

In use, device 10 is positioned so that one of shields 12, 14 serves as a base and the other is between the patient and the user's face, as shown in FIG. 1. Shield 12 serves as a base for device 10 if shield 14 is in the upper position (FIG. 1). Conversely, shield 14 is the base if shield 12 is in the upper position (FIG. 2). The patient's arm (or some other portion of the body on which a medical procedure is to be performed) is positioned in region 54, resting on either shield 12 or 14 (shield 12 in FIG. 1 ). First edges 24, 26 and second sides 22, 32 are oriented to shield the user's face while allowing relatively unobstructed access to region 54 for performing the procedure.

As will be evident from FIGS. 1 and 2, device 10 is symmetric. Shields 12 and 14 are oriented with respect to each other so either can serve as a base or support for the other and either serve as a shield. Also, support 16 holds shields 12 and 14 in cantilevered relationship so that access to the interior space between shields 12 and 14 is generally from the side opposite support 16. Consequently, the user can position device 10 on either arm of a patient regardless of the hand preference of the user, and orienting support 16 so that access for that user is most comfortable for his or her hand preference.

In use, device 10 is positioned so that the patient's arm is in region 54. Device 10 may be positioned for convenient access by a right-handed or left-handed user simply by selecting shield 12 or shield 14 as a base. After being positioned to suit the user's handedness, device 10 reduces the possibility of such fluids spraying, splashing, and so forth onto the user. However, device 10 allows the user a clear view and generally unobstructed working access to the patient. Region 54 is readily accessible, except for the access blocked by support 16. Access is maximized when cutout portions 50, 52 in support 16 are made.

To use device 10, assemble the needed equipment and proceed generally as follows:

1. Position the patient for best exposure of the site where the procedure is to be performed. The preferred position depends on the site and the procedure. Thus, for drawing blood from the antecubital fossa or the radial artery the patient may be in a sitting or a reclining position. For placing an arterial catheter in the radial artery or positioning an intravenous catheter, a reclining position is usually chosen.

Some practitioners may prefer to use protective gloves throughout the procedure; others may don gloves after palpation of the vein or artery, or at some other stage before skin penetration.

2. Position device 10 so that either shield 12 or 14 is over the site, between the site and the user's face, and the other shield is on a generally horizontal surface. Device 10 is preferably positioned so that line 62, drawn between the site and the user's face, is approximately perpendicular to the upper shield, that is, the upper shield is approximately parallel to the user's face.

As noted above, device 10 can readily accommodate both right- and left-handed access as well as different working styles. Thus, access region 54 is positioned on either the internal or external aspect of the site, depending on the preference of the user. Device 10 may be placed at any time during the procedure, as long as the device is in position prior to skin penetration.

3. Apply a tourniquet 64 several inches (usually 5–6 inches, or about 13–15 cm) proximal to the chosen site. Tourniquet 64 should be elastic and applied firmly, but not so tight as to occlude arterial pressure.
4. Palpate the site until an appropriate vein or artery can be felt.
5. Prepare the puncture site with an appropriate antiseptic and wait for the antiseptic to dry.
6. Carry out the desired procedure with device 10 in place.

Device 10 can be used for many common procedures, including venipuncture, arterial puncture, catheterization, and so forth. Device 10 can also be used for minor surgical procedures such as debridement of wounds or stitching incisions. Some nonlimiting examples of use of device 10 are:

I. Venipuncture For Blood Collection.

After preparing the site and positioning device 10 as described above, penetrate the skin with a sterile blood collection needle and advance the needle into the vein. Collect the blood using a syringe, a blood tube with a vacuum collector, or some other appropriate blood collection device. When the desired amount of blood has been withdrawn, release the tourniquet. Place a dry, sterile gauze pad over the site and remove the needle in a smooth, quick motion. Apply pressure to the site until bleeding is controlled. Remove device 10 and apply a bandage to the site if desired. Alternatively, apply a bandage before removing device 10.

II. Venipuncture For Administration of Terapeutic Intravenous. Agents.

The procedure provides a venous access for providing therapeutic intravenous agents such as fluids, nutritional supplements, blood components, or medications. The following procedure describes placement of an indwelling catheter. The procedure for an indwelling needle placement is similar but does not involve a stylet or catheter.

After preparing the patient and positioning device 10, penetrate the skin with a sterile catheter unit with stylet firmly in place, and advance the catheter until blood return is noted. Advance the catheter over the stylet and into the vein. Release the tourniquet, remove the stylet completely, and connect the catheter to an intravenous setup. Initiate the fluid flow and watch closely for signs of infiltration. If the flow is adequate and no problems are found, treat and secure the catheter as usual. Remove device 10.

When the procedure is completed, reposition device 10. Place a sterile dry gauze pad over the indwelling catheter and remove the catheter in a quick, smooth motion. Hold the site until bleeding has stopped. Remove device 10 and apply a bandage to the site. Alternatively, apply a bandage before removing device 10.

III. Arterial Puncture For Blood Collection.

Arterial puncture is undertaken for blood-collection purposes, especially in relation to obtaining blood-gas measurements. The following procedure is for drawing blood from the radial artery. Drawing blood from other extremity sites is similar with the exception of positioning the patient.

Before positioning device 10, ensure that there is adequate arterial flow to the hand (or other site). Position device 10 so that either shield 12 or 14 is over the site, between the site and the user's face. Penetrate the skin with a sterile arterial blood-collection device and advance into the artery. Collect the blood sample, then place a dry sterile gauze pad over the site and remove the blood-collection device in a smooth, quick motion. Apply pressure to the site for at least 10 minutes until the bleeding is controlled. Apply a dressing to the site and remove device 10.

IV. Arterial Puncture For Constant Blood Pressure Monitoring

The following description relates to placing an arterial catheter in the radial artery.

Before positioning device 10, ensure adequate arterial flow to the hand. Connect a syringe with appropriate flush solution to the catheter; flush the catheter. Position device 10 as described above. Penetrate the skin with a sterile catheter unit with stylet firmly in place, and advance into the artery until artery puncture is felt. Advance the catheter over the stylet and into the artery. Remove the stylet completely, and immediately connect the catheter to an arterial pressure monitoring apparatus. If no problems are found, treat and secure the catheter according to standard procedures and remove device 10.

To remove the catheter, position device 10 as described above. Place a sterile dry gauze pad over the indwelling catheter and remove the catheter in a quick, smooth motion. Hold the site for at least 10 minutes until bleeding has stopped. Apply a dressing and remove device 10.

It will be understood that the steps in the above descriptions may be varied depending on the procedure, the needs of the patient, and the preferences of the medical practitioner.

Device 10 may be used with any medical procedure that involves the collection of blood or other body fluids, venipuncture for the administration of therapeutic intravenous agents, arterial puncture, catheterization, and minor surgical procedures such as debridement or incision dressing. Device 10 is a nonintrusive device for improving the safety of procedures where the possibility of exposure to infectious or contagious body fluids exists, particularly procedures carried out on the patient's extremities.

It will be apparent to those skilled in the art that many changes and substitutions can be made to the preferred embodiment herein described without departing from the spirit and scope of the present invention as defined by the appended claims.

What is claimed is:

1. A device for use by a user in performing a medical procedure on a body, said device comprising:
   a first shield;
   a second shield; and
   means for holding said first and said second shields so as to define a space therebetween dimensioned for the body to be positioned in said space and to allow the user access to said space so that the medical procedure can be performed on the body, said device being orientable so that either said first shield or said second shield can be positioned between the user and the body so that the user is shielded from fluids from the body said first shield and said second shield held by said holding means so that said first ends of said first and second shields are closer to one another than said second ends of said first and second shields.

2. The device as recited in claim 1, wherein said holding means holds said first shield at an angle greater than 0 degrees with respect to said second shield.

3. The device as recited in claim 1, wherein said holding means holds said first shield at an angle in the approximate range of 15 degrees to 75 degrees with respect to said second shield.

4. The device as recited in claim 1, wherein said holding means holds said first shield and said second shield in cantilevered relation.

5. The device as recited in claim 1, wherein said holding means holds said first shield at an angle greater than 0 degrees and in cantilevered relation with respect to said second shield.

6. The device as recited in claim 1, wherein said device is made of a transparent material.

7. The device as recited in claim 1, wherein said device is made of a sterilizable material.

8. The device as recited in claim 1, wherein said device is made of a transparent, sterilizable material.

9. A device for use by a user in performing a medical procedure on a body, said device comprising:
   a first shield having a first end and an opposing second end, and a first side and an opposing second side and an opposing second side;
   a second shield having a first end and an opposing second end, and a first side and an opposing second side; and
   means for holding said first sides of said first and said second so as to define a space between said shields dimensioned for the body to be positioned said holding means allowing user access to said space so that the medical procedure can be performed on the body, said first shield and said second shield held so that said first ends of said first and second shields are spaced closer to one another than said second ends of said first and second shields.

10. The device as recited in claim 9, wherein said holding means holds said first shield at an angle to said second shield, said angle being greater than 0 degrees.

11. The device as recited in claim 9, wherein said holding means holds said first shield at an angle in the approximate range of 15 degrees to 75 degrees with respect to said second shield.

12. The device as recited in claim 9, wherein said holding means further comprises a support having a first side and an opposing second side, said first side of said support attached to said first side of said first shield and said second side of said support attached to said first side of said second shield.

13. The device as recited in claim 9, wherein said device is made of a transparent material.

14. The device as recited in claim 9, wherein said device is made of a sterilizable material.

15. The device as recited in claim 9, wherein said device is made of a transparent, sterilizable material.

16. A device for use by a user in performing a medical procedure on a body, said device comprising:
   a transparent first shield having a first end and an opposing second end, and a first side and an opposing second side;
   a transparent second shield having a first end and an opposing second end, and a first side and an opposing second side; and
   a support having a first side and a second side, said first side of said support attached to said first side of said first shield and said second side of said support attached to said first side of said second shield so as to define a space between said first and said second shields, said space dimensioned for receiving the body for positioning therein, the user having access to said space from said second sides of said first and said second shields and from said first and second ends of said first and said second shields so that the medical procedure can be performed on the body, said support holding said first shield and said second shield so that said first ends of said first and second shields are closer to one another than said second ends of said first and second shields.

17. The device as recited in claim 16, wherein said support and said first and second shields are integrally attached to each other.

18. The device as recited in claim 16, wherein said first shield and said second shield are held at an angle with respect to each other, said angle being in the range of 15 degrees to 75 degrees.

19. The device as recited in claim 16, wherein said support has a middle between said first and said second sides, said middle being narrower than said first and said second sides.

20. The device as recited in claim 16, wherein said device is made of a transparent material.

* * * * *